United States Patent [19]
Felsenstein et al.

[11] Patent Number: 5,703,129
[45] Date of Patent: Dec. 30, 1997

[54] 5-AMINO-6-CYCLOHEXYL-4-HYDROXY-HEXANAMIDE DERIVATIVES AS INHIBITORS OF β-AMYLOID PROTEIN PRODUCTION

[75] Inventors: Kevin Felsenstein; David W. Smith, both of Madison, Conn.; Michael A. Poss, Lawrenceville, N.J.; Prasad Chaturvedula, Cheshire; Charles P. Sloan, Wallingford, both of Conn.

[73] Assignee: Bristol-Myers Squibb Company, New York, N.Y.

[21] Appl. No.: 723,488

[22] Filed: Sep. 30, 1996

[51] Int. Cl.⁶ .................................................. A61K 31/17
[52] U.S. Cl. .................... 514/613; 514/620; 514/623; 564/156; 564/188; 564/191
[58] Field of Search .................................. 514/613, 623, 514/620; 564/156, 188, 191

[56] References Cited

FOREIGN PATENT DOCUMENTS

| | | | |
|---|---|---|---|
| 2005337 | 6/1990 | Canada. | |
| 652009A1 | 1/1985 | European Pat. Off. | 514/620 |
| 0212903A | 3/1987 | European Pat. Off. | |
| WO8904833 | 6/1989 | WIPO. | |
| WO 94/13319 | 10/1994 | WIPO | 514/620 |
| WO 95/09838 | 9/1995 | WIPO | 514/620 |

*Primary Examiner*—James H. Reamer
*Attorney, Agent, or Firm*—Richard P. Ryan

[57] ABSTRACT

A series of 5-amino-6-cyclohexyl-4-hydroxy-hexanamide derivatives of Formula I have been synthesized.

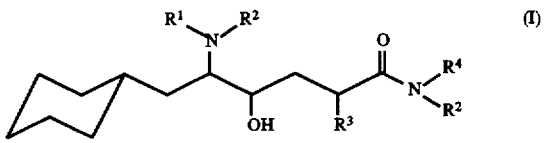

As inhibitors of the production of β-amyloid protein from β-amyloid precursor protein, these compounds are expected to be effective in treating patients suffering from or susceptible to conditions or disorders linked to brain accumulation of β-amyloid protein; e.g., Alzheimer's Disease and Down's Syndrome.

9 Claims, No Drawings

5-AMINO-6-CYCLOHEXYL-4-HYDROXY-HEXANAMIDE DERIVATIVES AS INHIBITORS OF β-AMYLOID PROTEIN PRODUCTION

BACKGROUND OF THE INVENTION

This invention generally pertains to novel organic compounds having drug and bio-affecting properties, their pharmaceutical compositions and method of use. In particular, the invention is concerned with 6-cyclohexyl-hexanamide derivatives. These compounds possess unique inhibition of γ-secretases, thereby acting to prevent the accumulation of amyloid protein deposits in the brain. More particularly, the present invention relates to the treatment of Alzheimer's Disease (AD).

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. There is currently no effective treatment.

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

The β-amyloid precursor protein (β-APP), a large membrane spanning glycoprotein found in tissues of mammals, including humans, is encoded by a gene on the long arm of human chromosome 21. The main constituent of the plaques, tangles and amyloid deposits is known as β-amyloid peptide (β-AP), an approximately 39 to 43 amino acid fragment of β-APP. Several lines of evidence support the involvement of β-AP in the pathogenesis of AD lesions. β-AP and related fragments have been shown to be toxic for PC-12 cell lines and primary cultures of neurons, as well as causing neuronal degeneration with accompanying amnesia in rodents. Strong evidence for the role of β-AP in AD consists of observations of genetic β-APP mutations in individuals with certain forms of Familial Alzheimer's Disease (FAD) and the correlation of disease onset with altered rates of release of β-AP fragments.

It is presently believed that the development of amyloid plaques in the brains of AD patients is a result of excess production and/or reduced clearance or removal of β-AP. It is known that a basal level of β-AP production may be a normal process and that multiple pathways for cleavage of β-APP exist. Currently, however, there is no consensus regarding classes of proteinases or inhibitors thereof that would be effective in treating AD. Various peptidergic compounds and their pharmaceutical compositions have been disclosed as useful in inhibiting or preventing amyloid protein deposits in brains of AD and Down's Syndrome patients.

Davey, et al in European Patent Application 652009A1 disclosed a series of polyamido inhibitors of aspartic proteases, e.g. cathepsin D, for use in inhibiting intracellular β-production.

A series of peptidergic compounds and their administration to patients to prevent abnormal deposition of β-AP was disclosed by Cardell, et al., in WO 95/09838 as a means of treating AD.

Tamburini, et al. in WO 94/13319 disclosed methods for regulating formation of β-AP by use of inhibitors of certain aspartic and serine proteases such as cathepsin D. Specifically, cathepsin D inhibitors were preferred. A series of peptidic compounds resembling pepstatin analogs was disclosed and claimed.

Nothing in these references can be construed to disclose or suggest the novel compounds of this invention and their use to inhibit β-AP production.

SUMMARY DESCRIPTION OF THE INVENTION

A series of 5-amino-6-cyclohexyl-4-hydroxy-hexanamide derivatives have been synthesized. These compounds specifically inhibit the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds to patients suffering from, or susceptible to, these conditions involves reducing β-AP available for accumulation and deposition in brains of these patients.

DETAILED DESCRIPTION OF THE INVENTION

The invention comprises compounds of Formula I, their pharmaceutical formulations, and their use in inhibiting β-AP production in patients suffering from or susceptible to AD or other disorders resulting from β-AP accumulation in brain tissue. The compounds of Formula I include pharmaceutically acceptable acid addition salts and/or hydrates.

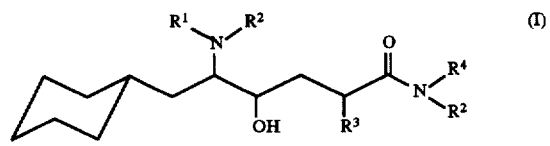

In Formula I, the symbols $R^1$–$R^4$ have the following meanings.

$R^1$ is selected from $C_{4-8}$ alkyl, $C_{4-8}$ alkenyl, lower alkoxy-lower-alkanediyl, $R^5$-substituted $C_{3-6}$ cycloalkyl, $R^5$-substituted $C_{3-6}$ cycloalkyl-lower-alkanediyl, and Ar—$(CH_2)_n$— groups. Ar can be $R^5$-substituted phenyl and naphthyl rings with $R^5$ being hydrogen, lower alkyl or alkoxy; and n is the integer 1 to 4. By "lower" is meant $C_{1-6}$ alkyl or alkoxy groups that may be straight chain or branched. $C_{4-8}$ alkyl comprises straight chain and branched, alkyl groups. Lower alkoxy-lower-alkanediyl means such groups as 1-methylethoxyethyl-$R^5$-substituted $C_{3-6}$ cycloalkyl would encompass rings from cyclopropane to cyclohexane bearing an $R^5$ substituent. These rings can also be connected to the nitrogen atom via a lower alkanediyl group.

$R^2$ is independently selected from hydrogen and methyl.

$R^3$ is selected from lower alkyl, $C_{3-6}$ cycloalkyl, $C_{3-6}$ cycloalkyl-lower-alkanediyl, $C_{3-6}$ alkenyl, and $Ar-CH_2)_n-$.

$R^4$ is selected from $R^3$, lower alkyl-thio-lower alkyl, and

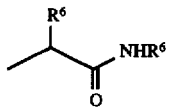

wherein $R^6$ is lower alkyl.

The compounds of the present invention can exist as stereoisomers, meaning that the individual isomers differ only in spatial orientation of their atoms and not in sequential structure. By "stereoisomers" is included enantiomers (mirror image isomers), geometric (cis/trans) isomers, and diastereomers (isomers having more than one chiral center and which are not mirror images of one another). The individual isomers, as well as racemic mixtures of isomers, are within the scope of the present invention. The racemic mixtures can be separated into their individual isomers through well-known techniques such as the separation of the diastereomeric salts formed with optically active acids, followed by conversion back to the optically active bases.

A preferred group of compounds have the stereochemistry indicated in Formula IA.

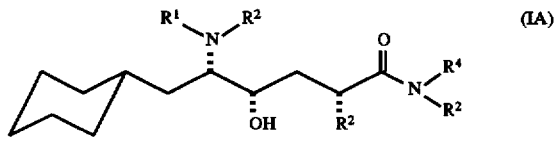

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like.

The compounds of the present invention may be produced by the processes shown in Schemes A and B. Scheme A illustrates the general processes, and Scheme B shows production of chiral compounds of Formula IA. In both schemes, $R^1-R^6$ are as previously defined. The abbreviation t-BOC refers to the t-butoxycarbonyl protecting group,

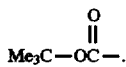

Another route from Formula VII chiral intermediates to Formula VI chiral compounds is shown in Scheme C. Other reagents shown in the schemes are familiar to those skilled in organic synthesis and their usage would be readily understood.

The penultimate intermediate (II) in Schemes A and B can be reached by two convergent pathways. Intermediate V compounds can be treated with $R^2,R^4$-disubstituted amines using the general procedure of Poss, et al., (*Tet. Lett.*, 1992, 33 (11), 1411–14) to convert the terminal alkyl ester group to the amide compound IV. Catalytic hydrogenation of the olefin bond provides intermediate III which is ring-opened with acid to yield compound II.

The other route utilizes starting from methyl 3-iodopropionate VIII and utilizing t-BOC-cyclohexylalaninal. Intermediate VII is alkylated using an $R^3$—Li agent and hexamethyldisilazide to give intermediate VI. Ring-opening amination with $HNR^2R^4$ then provides compound II.

The 5-amino substituent of compound II can either be alkylated with, e.g., an alkyl halide or reductively alkylated using a carbonyl compound and a sodium borohydride reagent to afford the subject cyclohexyl-hexanamide products of Formula I. Modification of these reaction schemes can be employed to produce Formula I compounds in somewhat different ways. For example, when the $R^3$-substituent in compound II contains an olefinic bond, an optional hydrogenation step can be utilized to convert the olefinic substituent to an aliphatic substituent before conversion of compound II into Formula I product. Specific syntheses will be provided infra in the Examples section and will provide additional guidance. Reagents, solvents and reaction conditions for the steps of these processes would be known to one skilled in organic synthesis as these steps comprise standard organic reactions, the details of which are readily available in the chemical literature.

Accumulating findings have led to the perception that compounds that demonstrate inhibition of the formation of β-AP from β-APP would be clinically efficacious in treating disorders such as Alzheimer's Disease, Down's Syndrome, and certain forms of brain degeneration. In this regard, the compounds of the instant invention demonstrate potent inhibition of β-AP formation. These compounds also demonstrate inhibition of β-APP cleavage at the γ-secretase site and this action is believed to be related to the reduction in β-AP formation observed.

Representative compounds of the instant series have been tested for their ability to inhibit γ-secretase cleavage. Results of this screening assay are shown in Table 2 in the Example section.

Another aspect then of the instant invention provides a method for treating an Alzheimer's or Down's sufferer which comprises systemic administration to the sufferer of a therapeutically effective amount of a compound of Formula I or a pharmaceutically acceptable salt thereof.

The administration and dosage regimen of compounds of Formula I would be in accord with the degree of β-AP inhibition sought. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, intra-nasal, rectal and parenteral (i.e. intramuscular, intravenous and subcutaneous). Generally, it will be found that when a compound of the present invention is administered orally, a larger quantity of the active agent is required to produce the same effect as a smaller quantity given intra-nasally, parenterally or transdermally. In accordance with good clinical practice, it is preferred to administer the instant compounds at a concentration level that will produce effective antimigraine effects without causing any harmful or untoward side effects.

The compounds of the present invention may be administered for anti-amyloid purposes either as individual therapeutic agents or as mixtures with other therapeutic agents. Therapeutically, they are generally given as pharmaceutical compositions comprised of an anti-amyloid amount of a compound of Formula I or a pharmaceutically acceptable salt thereof and a pharmaceutically acceptable carrier, excipient or diluent thereof. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts (δ) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), triplet (t) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight. Mass spectral (MS) characteristics were determined using electrospray ionization and desorption chemical ionization.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent.

DESCRIPTION OF SPECIFIC EMBODIMENTS

A. Preparation of Intermediate Compounds

Some representative procedures for preparation of synthetic intermediate compounds utilized in the processes of Schemes A and B are given hereinbelow. Some starting materials and intermediates (e.g. Formulas VIII compounds), am either commercially available or procedures for their synthesis are readily available to the chemical literature allowing their full utilization by one skilled in the art of organic synthetic chemistry. To illustrate stereochemical outcomes, the examples include chiral compounds and processes.

EXAMPLE 1

Methyl 3-iodopropionate (VIII)

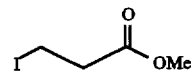

A mixture of methyl 3-bromopropionate (20.00 g, 119.75 mmol) and sodium iodide (45 g, 299.38 mmol) in acetone (600 mL) was heated at reflux for 16 h. The solvent was removed in vacuo and the residue was extracted with hexane (500 mL) and water (200 mL). The aqueous layer was extracted with additional hexane (200 mL). The combined organic layers were washed with 20% aqueous sodium thiosulfate (200 mL) and then with brine, dried with MgSO$_4$, filtered and concentrated in vacuo to give 21.18 g (98.97 mmol, 83%) of the title compound as a colorless liquid.

EXAMPLE 2

[1S-[1R*,2α(R*)]][2-cyclohexyl-1-[tetrahydro-5-oxo-2-furanyl]ethyl]carbamic acid, 1,1-dimethylethyl ester (VII)

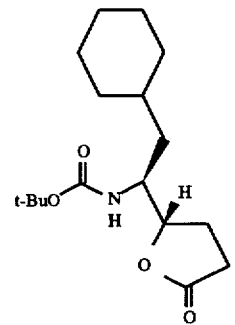

A modified procedure of DeCamp, A. E., Kawaguchi, A. T., Volante, R. P. and Shinkai, I. (Tet. Lett. 1991, 32 (16), 1867–70) was used. Methyl 3-iodopropionate (Example 1: 48.95 g, 228.76 mmol), zinc-copper couple (29.74 g, 457.52 mmol), anhydrous toluene (450 mL) and dimethylacetamide (45 mL) were stirred for 1 h at r.t. then 1.5 h at 80° C. while under N$_2$ atmosphere. The mixture was cooled to r.t. and the excess zinc-copper couple allowed to settle. A solution of anhydrous toluene (50 mL), dry CH$_2$Cl$_2$ (250 mL) and Ti(OiPr)$_4$ (14.71 mL, 49.82 mmol) in a mechanically stirred flask was cooled to 15° C. and TiCl$_4$ (16.39 mL, 149.48 mmol) was added dropwise (while maintaining the reaction temperature below 25° C.) to form a pale yellow solution of TiCl$_3$(OiPr) which was stirred at r.t. for 15 min and then cooled to –40° C. The supernatant from the reaction of methyl 3-iodopropionate and Zn—Cu prepared above was added by cannula to the solution containing TiCl$_3$(OiPr) while not allowing the reaction mixture to exceed –20° C. After the addition was complete, the reaction was stirred at –25° C. for 5 min then cooled –40° C. A solution of t-Boc-(S)-cyclohexylalaninal (25.41 g, 99.65 mmol) in CH$_2$Cl$_2$ (100 mL) was added by cannula to the reaction while maintaining the reaction temperature below –35° C. After the addition was complete, the reaction mixture was stirred vigorously at –20° C. for 16 h. The reaction was quenched by the addition of water (500 mL) and then ethyl ether (500 mL) at 0° C. The mixture was stirred for 15 min. The aqueous phase was separated and extracted with ethyl ether (500 mL). The combined organic phases were washed sequentially with water, sat. aqueous NaHCO$_3$, water and brine. The organic phase was dried (MgSO$_4$), filtered and concentrated in vacuo. The concentrate was dissolved in toluene (900 mL) and glacial AcOH (30 mL) and heated at reflux for 3 hr. The mixture was cooled to r.t., diluted with EtOAc and washed sequentially with water (500 mL), sat. aqueous NaHCO$_3$, water and brine. The organic phase was dried (MgSO$_4$), filtered and evaporated in vacuo. Silica gel chromatography (4:4:0 to 4:4:2 hexane:CH$_2$Cl$_2$:EtOAc gradient) of the concentrate afforded 12.65 g (40.86 mmol, 41%) of the title compound as a white amorphous solid. MS (ESI) m/e 329 (M+NH$_4$)$^+$; m/e 304 (M−H)$^-$.

EXAMPLE 3

[1S-[1R*,2α(R*),4β(R*)]][2-Cyclohexyl-1-[tetrahydro-4-methyl-5-oxo-2-furanyl]ethyl]carbamic acid, 1,1-dimethylethyl ester (VI)

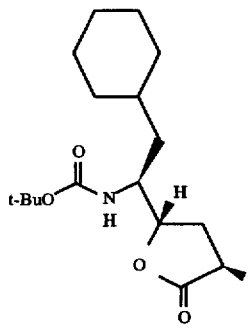

A solution of hexamethyldisilazide (0.75 mL, 3.54 mmol) in dry THF (2.5 mL) was cooled to 0° C. and 2.2M n-BuLi in hexane (1.53 mL, 3.38 mmol) was added dropwise over 5 min. After the addition was complete, the reaction was allowed to warm to r.t. and stand for 15 min. The solution was cooled to −78° C. and [1S-[1R*,2α(R*)]][2-cyclohexyl-1-[tetrahydro-5-oxo-2-furanyl]ethyl]carbamic acid, 1,1-dimethylethyl ester (0.5 g, 1.61 mmol) in THF (5 mL) was added dropwise over 5 min. The mixture was stirred at −78° C. for 30 min and methyl iodide (0.23 g, 1.61 mmol) in THF (2 mL) was added dropwise over 2 min. After the addition was complete the reaction was stirred at −78° C. for 30 min and then quenched with propionic acid (0.4 mL) in THF (2 mL). After stirring for 5 min the reaction was allowed to warm to r.t. and stand for 15 min. Aqueous 10% citric acid (20 mL) and EtOAc (100 mL) were added and the two phases were separated. The aqueous phase was extracted with EtOAc (60 mL). The combined organic layers were washed with sat. aqueous NaHCO$_3$, brine, dried with Na$_2$SO$_4$, filtered, and concentrated in vacuo. Silica gel chromatography (4:4:0 to 4:4:2 hexane:CH$_2$Cl$_2$:EtOAc gradient) of the concentrate provided the title compound (0.20 g, 38%) as a white amorphous solid.

Using the procedure of Example 3 with appropriate modifications, various Formula VI compounds can be prepared via lithiation of a Formula VII compound, e.g. Example 2, followed by alkylation with selected electrophilic reagents. While catalytic hydrogenation of R$^3$=alkenyl Formula VI compounds would provide alkyl R$^3$-substituted Formula VI compounds, in practice the olefin-containing VI compounds were ring opened with NHR$^2$R$^4$/HOAc to give the compound II product and then the olefinic R$^3$-substituent was hydrogenated to produce the R$^3$=alkanyl Formula II compound for carrying on to product I. The hydrogenation sequence to give Formula II compounds is shown in Table 1.

TABLE 1

Hydrogenation of Formula VI Compounds

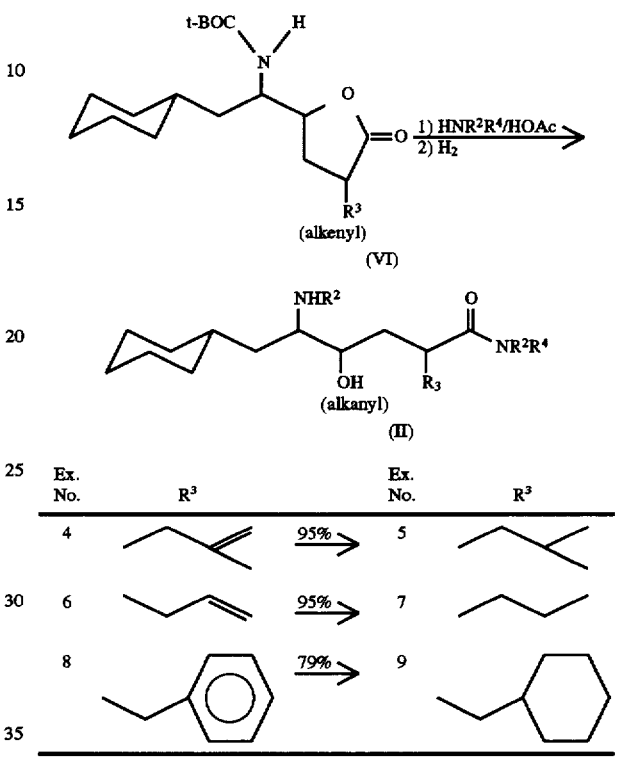

EXAMPLE 10

[1S-[1R*,2α(R*),4β(R*)]][2-cyclohexyl-1-[tetrahydro-4-(1-hydroxy-1-methylethyl)-5-oxo-2-furanyl]ethyl]carbamic acid, 1,1-dimethyl ester (XVI)

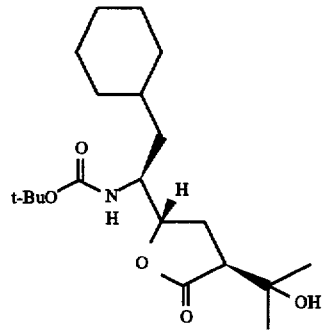

To freshly distilled THF (20 mL) at 0° C. was added diisopropylamine (1.98 mL, 14.12 mmol) followed by n-butyllithium (5.65 mL, 14.12 mmol). The reaction was stirred for five min and then cooled to −78° C. A solution of [1S-[1R*,2α(R*)]][2-cyclohexyl-1-[tetrahydro-5-oxo-2-furanyl]ethyl]carbamic acid, 1,1-dimethylethyl ester (Example 2; 2.0 g, 6.42 mmol) in dry THF (5 mL) was added over a period of two min and stirring continued for an additional 40 min. Dry acetone (1.04 mL, 14.16 mL) was added to the reaction mixture and stirred for 30 min. The reaction was quenched with a saturated aqueous solution of NH₄Cl. The reaction mixture was extracted with EtOAc. The combined organic extracts were washed sequentially with 10% citric acid, 5% aqueous NaHCO₃ and brine. The organic phase was dried with Na₂SO₄, filtered, and concentrated in vacuo. Silica gel chromatography (4:1 hexane:EtOAc) of the concentrate afforded the title compound (1.9 g, 80%) whose physical properties were in agreement with literature data (Morisawa, Y., Katoaka, M., Yabe, Y., Koike, H., Takahagi, H., Iijima, Y., Kokubu, T., Hiwada, K. Eur. Pat. Appl. EP 0383635 A2).

EXAMPLE 11

Ethanedioic acid, 1-[5-[2-cyclohexyl-1-[[1,1-dimethylethoxy)carbonyl]amino]ethyl]tetrahydro-2-oxo-3-furanyl]-1-methylethyl methyl ester [1S[1R*, 3β(R*), 5α(R*)]] (XXVI)

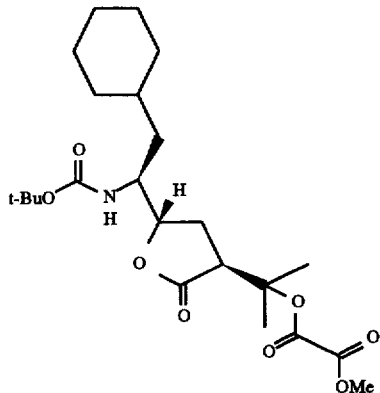

To a well stirred THF (15 mL) solution containing triethylamine (0.98 mL, 7.0 mmol), 4-(N,N-dimethylamino) pyridine (5 mg) and from Example 10 [1S-[1R*,2α(R*), 4β(R*)]][2-cyclohexyl-1-[tetrahydro-4-(1-hydroxy-1-methylethyl)-5-oxo-2-furanyl]ethyl]carbamic acid, 1,1-dimethyl ester (XVI: 1.3 g, 3.5 mmol) at 0° C. was added methyl oxalyl chloride (0.65 mL, 7.1 mmol). After the addition was complete, the reaction was allowed to warm to room temperature and stand for three h with stirring. The solvent was removed in vacuo and the residue was dissolved in EtOAc. The organic phase was washed with brine, dried (Na₂SO₄), filtered and concentrated in vacuo. Silica gel chromatography (4:1 hexane:EtOAc) of the concentrate afforded the title compound (1.44 g, 90%).

EXAMPLE 12

[1S-[1R*,2α(R*),4β(R*)]][2-cyclohexyl-1-[tetrahydro-4-(1-methylethyl)-5-oxo-2-furanyl]ethyl] carbamic acid, 1,1-dimethyl ester

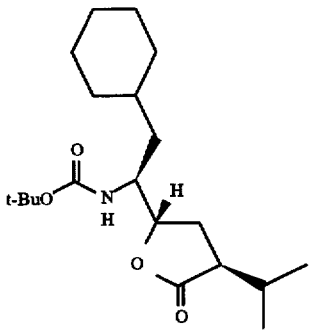

The product from Example 11, ethanedioic acid, 1-[5-[2-cyclohexyl-1-[[1,1-dimethylethoxy)carbonyl]amino]ethyl] tetrahydro-2-oxo-3-furanyl]-1-methylethyl methyl ester [1S [1R*,3β(R*),5α(R*)]], (XXVI: 1.0 g, 2.2 mmol) was dissolved in anhydrous toluene (10 mL) and heated to 110° C. A toluene (3.0 mL) solution containing tris(trimethylsilyl) silane (0.68 mL, 4.4 mmol) and azobis(isobutyronitrile) (150 mg) was added dropwise to the heated reaction over a period of five h. After the addition was complete, the reaction was refluxed for an additional two h. The solvent was removed in vacuo. Silica gel chromatography (95:5 hexane:EtOAc) of the concentrate afforded the title lactone compound (582 mg, 75%. The spectral properties agreed with the reported values (Nishi, et al., Chem. Lett. 1989, 11, 1993–6) and nOe experiments further confirmed the stereochemistry at the newly generated asymmetric center.

Using the procedure of Example 12 but employing cyclopentanone and 3-pentanone as the electrophilic reagent gives example compounds 13 and 14.

EXAMPLE 13

[1S-[1R*,2α(R*),4β(R*)]][2-cyclohexyl-1-[tetrahydro-4-cyclopentyl-5-oxo-2-furanyl]ethyl] carbamic acid, 1,1-dimethyl ester

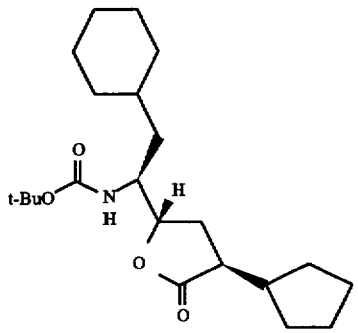

EXAMPLE 14

[1S-[1R*,2α(R*),4β(R*)]][2-cyclohexyl-4-(1-ethylpropyl)-1-[tetrahydro-5-oxo-2-furanyl]ethyl] carbamic acid, 1,1-dimethyl ester

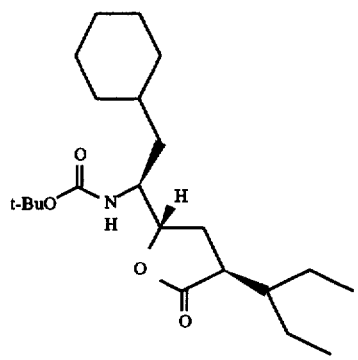

EXAMPLE 15

5-[2-[(Butylamino)carbonyl]-3-methyl-1-butenyl]-4-(cyclohexylmethyl)-2,2-dimethyl-3-oxazolidinecarboxylic acid, 1,1-dimethylethyl ester (V)

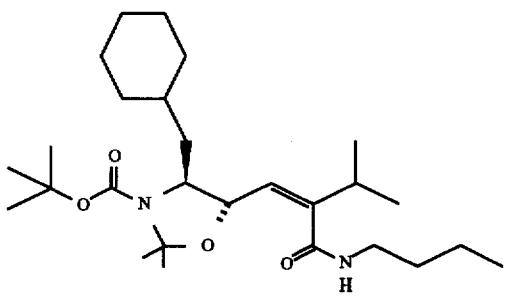

The procedure of Poss, M. A. and Reid, J. A. (*Tet. Lett.* 1992, 33 (11), 1411–14) was used. A 2.0M solution of trimethylaluminum (1.25 mL, 2.5 mmol) in hexane was added to a 1,2-dichloroethane (1.25 mL) solution containing butylamine (0.25 mL, 2.5 mmol) at r.t. and stirred for one h. A 1,2-dichloroethane (1.25 mL) solution containing 5-[2-[(ethoxy)carbonyl]-3-methyl-1-butenyl]-4-(cyclohexylmethyl)-2,2-dimethyl-3-oxazolidinecarboxylic acid, 1,1-dimethylethyl ester (424 mg, 1.0 mmol) was added to the reactants prepared above and heated at 70° C. for 16 h. The reaction was cooled to 0° C., diluted with CHCl₃, and treated with 1N HCl. The organic phase was separated and the aqueous phase extracted with CHCl₃ (2×). The combined organic extracts were dried (Na₂SO₄), filtered through MgSO₄ and concentrated in vacuo. Silica gel chromatography (5:1 hexane:Et₂O) of the concentrate afforded the title compound (408 mg, 88%). MS (ESI) m/e 463 (M−H)⁻.

EXAMPLE 16

5-[2-[(Butylamino)carbonyl]-3-methylbutyl]-4-(cyclohexylmethyl)-2,2-dimethyl-3-oxazolidinecarboxylic acid, 1,1-dimethylethyl ester (IV)

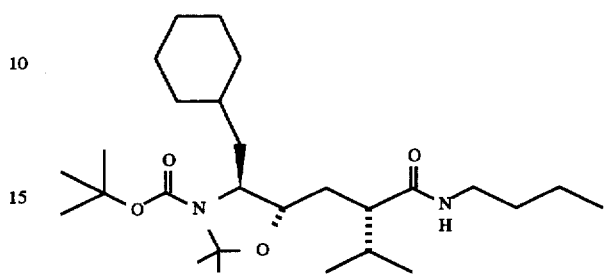

A THF (2.03 mL) solution containing 5-[2-[(butylamino)carbonyl]-3-methyl-1-butenyl]-4-(cyclohexylmethyl)-2,2-dimethyl-3-oxazolidinecarboxylic acid, 1,1-dimethylethyl ester (236 mg, 0.51 mmol) and rhodium on alumina (24 mg, 10% by wt, 5% Rh content) was placed under a hydrogen atmosphere for 16 h. Additional rhodium on alumina (24 mg) in THF (2.03 mL) was added and the reaction continued under H₂ atmosphere for 6 h. The mixture was diluted with CHCl₃, filtered and concentrated in vacuo. Silica gel chromatography (3:1 to 3:2 hexane:Et₂O gradient) of the concentrate afforded the title compound (171 mg, 70%). MS (ESI) m/e 465 (M−H)⁻ MS (ESI) m/e 467 (M+H)⁺.

EXAMPLE 17

[αS-(αR*,γR*,δR*)]δ-Amino-N-butyl-γ-hydroxy-α-(1-methylethyl)-cyclohexanehexanamide hydrochloride (II)

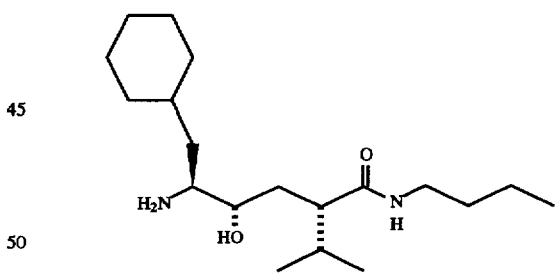

5-[2-[(Butylamino)carbonyl]-3-methylbutyl]-4-(cyclohexylmethyl)-2,2-dimethyl-3-oxazolidinecarboxylic acid, 1,1-dimethylethyl ester (171 mg, 0.366 mmol) was dissolved in an HCl/dioxane solution (1.37 mL, 4N HCl) at 0° C. and allowed to stand for two h. The solution was concentrated in vacuo. Silica gel chromatography (35:5:0.1 CH₂Cl₂:MeOH:NH₄OH) of the concentrate afforded the title compound as the free base (88.5 mg, 74%) which was subsequently converted to the hydrochloride salt. The free base was dissolved in MeOH (10 mL) and treated with 1N HCl (0.27 mL) for one h. The reaction was concentrated in vacuo, diluted with water, filtered and lyophilized to afford the title compound (72 mg, 54%).

EXAMPLE 18

δ-Amino-N-butyl-γ-hydroxy-α-methyl-cyclohexanehexanamide (II)

A. [1S-(1R*,2R*,4R*)][5-(Butylamino)-1-(cyclohexylmethyl)-2-hydroxy-4-methyl-5-oxopentyl] carbamic acid, 1,1-dimethylethyl ester

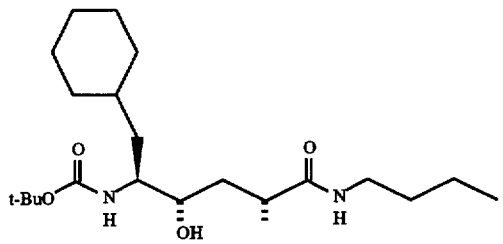

To a solution of [1S-[1R*,2α(R*),4β(R*)]][2-cyclohexyl-1-[tetrahydro-4-methyl-5-oxo-2-furanyl]ethyl]carbamic acid, 1,1-dimethylethyl ester (0.20 g, 0.62 mmol) in n-BuNH$_2$ (5.78 mL, 58.46 mmol) was added glacial acetic acid (1.10 mL) and heated at reflux for 1.5 h. The reaction mixture was cooled to r.t. and diluted with CH$_2$Cl$_2$ and 10% aqueous K$_2$CO$_3$. The organic layer was washed with water, brine, dried (MgSO$_4$), filtered and concentrated in vacuo. Silica gel chromatography (95:5:0.5 CH$_2$Cl$_2$:MeOH:NH$_4$OH) of the concentrate afforded the title compound (0.23 g, 93%).

B. [αS-(αR*,γR*,δR*)]δ-Amino-N-butyl-γ-hydroxy-α-methyl-cyclohexanehexanamide (II)

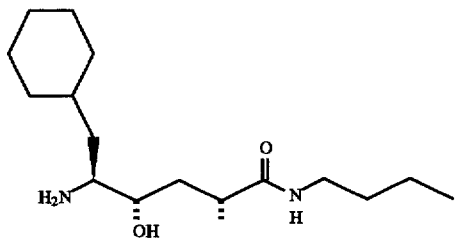

A solution of the product from A [1S-(1R*,2R*, 4R*)][5-(butylamino)-1-(cyclohexylmethyl)-2-hydroxy-4-methyl-5-oxopentyl]carbamic acid, 1,1-dimethylethyl ester (0.23 g, 0.58 mmol) in dioxane (5 mL) at 0° C. was added a dioxane solution (15 mL) saturated with HCl(g) and allowed to stand two h and then warm to r.t. for 16 h. The reaction was made basic (pH=8) by the dropwise addition of conc. NH$_4$OH and then extracted with CH$_2$Cl$_2$. The organic layer was washed with water, dried (Na$_2$CO$_3$), filtered and concentrated in vacuo. Silica gel chromatography (90:10:1 CH$_2$Cl$_2$:MeOH:NH$_4$OH) of the concentrate afforded the title compound (0.20 g, 98%).

B. Synthesis of Formula I Products

EXAMPLE 19

[αS-(αR*,γR*,δR*)]N-Butyl-γ-hydroxy-α-methyl-δ-[(4-methylpentyl)amino]cyclohexanehexanamide hydrochloride

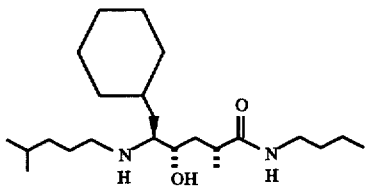

To a solution of [αS-(αR*,γR*,δR*)]δ-amino-N-butyl-γ-hydroxy-α-methyl-cyclohexanehexanamide (II: 0.17 g, 0.57 mmol) and 4-methylvaleraldehyde (0.063 g, 0.63 mmol) in CH$_2$Cl$_2$ (3 mL) was added NaBH(OAc)$_3$ (0.181 g, 0.86 mmol) and glacial acetic acid (0.05 mL). The mixture was stirred at r.t. for 16 h. The reaction was made basic (pH=8) by the addition of sat aqueous NaHCO$_3$ and extracted with CH$_2$Cl$_2$. The organic extracts were washed with brine, dried (Na$_2$SO$_4$), filtered and concentrated in vacuo. Silica gel chromatography (19:19:1 0.05 CHCl$_3$:Et$_2$O:MeOH:NH$_4$OH) of the concentrate gave the free amine (0.128 g, 59%) which was converted to its hydrochloride salt by the addition of 1.5N ethanolic HCl (0.3 mL). Removal of solvent in vacuo gave the title compound (0.128 g, 59%) as an amorphous white solid, mp 65° C.

$^1$H NMR (DMSO d$_6$) d 0.86 (d, j=7.2, 12H), 1.1 (d, j=6.9, 3H), 1.15–1.17 (q, j=7.3, 5H), 1.23–1.30 (m, 10H), 1.42–1.7 (m, 11H), 2.47 (s, 3H), 2.56 (bs, 1H), 2.83 (bd, j=6.75, 3H), 2.94–3.07 (m, 2H), 3.32 (s, 3H), 3.40 (bs, 1H), 5.67 (d, j=6, 1H), 8.03 (bt, j=5.5, 2H), 8.3 (bs, 1H). MS (ESI) m/e 383 (MH)$^+$. Anal. Calcd. for C$_{23}$H$_{46}$N$_2$O$_2$.1. 1.1 HCl. 0.2 H$_2$O: C, 65.36; H, 11.30; N, 6.63. Found: C, 65.56; H, 11.68; N, 6.25.

EXAMPLE 20

[αS-(αR*,γR*,δR*)]N-Butyl-γ-hydroxy-α-(1-methylethyl)-δ-[(4-methylpentyl)amino]cyclohexanehexanamide hydrochloride

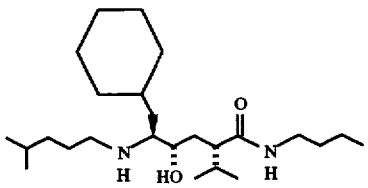

[αS-(αR*,γR*,δR*)]δ-Amino-N-butyl-γ-hydroxy-α-(1-methylethyl)cyclohexanehexanamide hydrochloride (II: 152 mg, 0.328 mmol), sodium acetate (27 mg, 0.328 mmol) and 4-methylpentanal (36 mg, 0.36 mmol) were dissolved in MeOH (3.2 mL). Sodium cyanoborohydride (20.6 mg, 0.328 mmol) was added and the reaction cooled to 0° C. Acetic acid (0.57 mL, 10.0 mmol) was added dropwise. After the addition was complete the reaction was allowed to warm to r.t. over 3 h. Additional acetic acid was added (0.3 mL) and the reaction was allowed to continue for 30 min. The reaction was brought to a pH of one by the addition of 1N HCl and continued stirring for one h. Water (10 mL) was added and the reaction was neutralized by the addition of solid NaHCO₃. The aqueous phase was extracted with CHCl₃ (3×15 mL). The combined organic extracts were dried (MgSO₄), filtered and concentrated in vacuo. Silica gel chromatography (97.5:2.5:0.2 to 96:4:0.2 CH₂Cl₂:MeOH:NH₄OH gradient) of the concentrate afforded the free amine (76 mg, 56%) which was converted to the hydrochloride salt by treating a MeOH (5 mL) solution of the amine with 1N HCl (0.185 mL). The solvent was removed in vacuo and the residue dissolved in water (20 mL) and EtOH (2 mL). Filtration and lyophilization afforded the title compound (84 mg, 56%) as a white solid.

mp 74°–76° C.; IR (KBr): 3424, 2960, 2854, 1638, 1450, 1388, 1168, 1020 cm⁻¹; MS (ES), 411 (M+H)⁺.

A number of additional Formula I products were prepared by reacting Formula VI intermediates with primary amines (as in Example 18A) followed by removal of the 5-butoxycarbonyl protecting group (as in Example 18B) to give Formula II intermediates. These Formula II compounds are then reductively aminated with appropriate aldehydes to afford to the Formula I products.

EXAMPLE 21

[αS-(αR*,γR*,δR*)]N-Butyl-γ-hydroxy-α-(2-methyl-2-propenyl)-δ-[(4-methylpentyl)amino] cyclohexanehexanamide hydrochloride

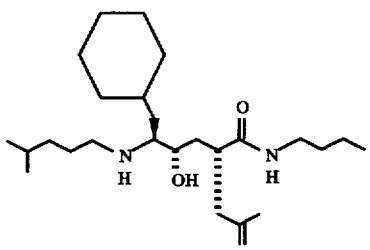

Prepared by reaction of the Example 4 product with butylamine and then 4-methyl-valeraldehyde.

Yield=45%; oil; IR (KBr): 3276, 3074, 1644, 1554, 1466, 1378 1150, 1058 cm⁻¹; MS (ES), 423 (M+H)⁺.

EXAMPLE 22

[αS-(αR*,γR*,δR*)]N-Butyl-γ-hydroxy-δ-[(4-methylpentyl)amino]-α-(2-methylpropyl) cyclohexanehexanamide hydrochloride

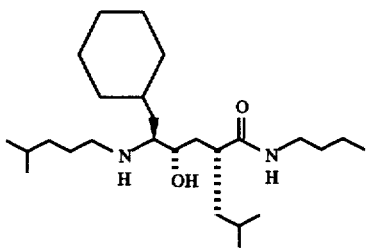

Prepared by reaction of the Example 5 product in the same manner as Example 21.

Yield=56%; mp 78°–80° C.; IR (KBr): 3278, 2870, 1782, 1640, 1468, 1386, 1308, 1228, 1060, 964 cm⁻¹; MS (ES), 425 (M+H)⁺.

EXAMPLE 23

[αS-(αR*,γR*,δR*)]N-Butyl-γ-hydroxy-δ-[(4-methylpentyl)amino]-α-(2-propenyl) cyclohexanehexanamide hydrochloride

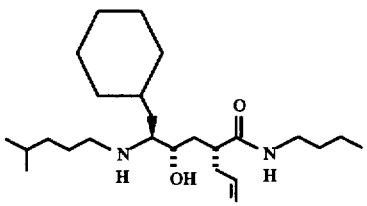

Prepared as in Example 21 but starting with Example 6 product.

Yield=55%; oil; IR (KBr): 3276, 3076, 1642, 1554, 1466, 1386, 1368, 1254, 1150, 994 cm⁻¹; MS (ES), 409 (M+H)⁺.

EXAMPLE 24

[αS-(αR*,γR*,δR*)]N-Butyl-γ-hydroxy-δ-[(4-methylpentyl)amino]-α-(2-propyl) cyclohexanehexanamide hydrochloride

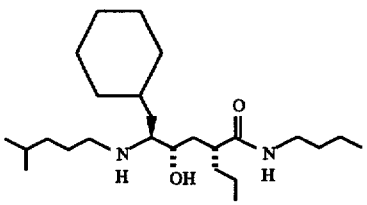

Prepared according to Example 21 starting with Example 7 product.

Yield=53%; oil; IR (KBr): 3276, 2872, 1640, 1554, 1466, 1450, 1386, 1298, 1152, 1046, 752 cm⁻¹; MS (ES), 411 (M+H)⁺.

EXAMPLE 25

[αS-(αR*,γR*,δR*)]N-Butyl-γ-hydroxy-δ-[(4-methylpentyl)amino]-α-(phenylmethyl) cyclohexanehexanamide hydrochloride

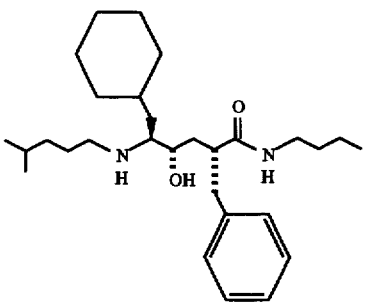

Prepared according to Example 21 starting with Example 8 product.

Yield=51%; mp 67° C.: IR (KBr) 3292, 2958, 2928, 2854, 1640, 1450 cm⁻¹; MS (ES), 459(M+H)⁺.

EXAMPLE 26

[αS-(αR*,γR*,δR*)]-N-Butyl-α-(cyclohexylmethyl)-γ-hydroxy-δ-[(4-methylpentyl)amino]cyclohexanehexanamide, hydrochloride

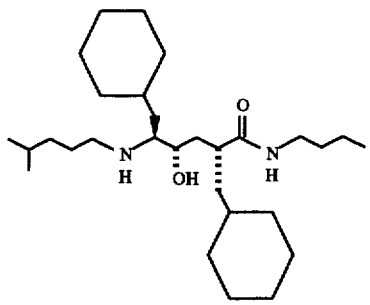

Yield=38%; mp 86° C.: IR (KBr) 3300, 2956, 2926, 2852, 1640, 1448 cm$^{-1}$; MS (ES), 465(M+H)$^+$.

EXAMPLE 27

[αS-(αR*,γR*,δR*)]-α-(cyclohexylmethyl)-N-(cyclopropylmethyl)-γ-hydroxy-δ-[(4-methylpentyl)amino]cyclohexanehexanamide hydrochloride

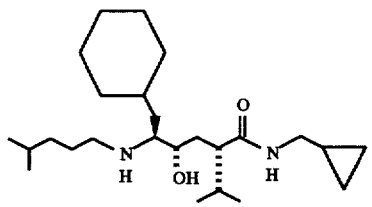

Prepared by reacting the Example 12 product with cyclopropylmethylamine followed by 4-methylvaleraldehyde as in Example 21.

Yield=60%; mp 74°-76° C.; IR (KBr) cm$^{-1}$; MS (ES), 409 (M+H)$^+$.

EXAMPLE 28

[αS-(αR*,γR*,δR*,N-(1S*))]γ-hydroxy-α-(1-methylethyl)-δ-[(4-methylpentyl)amino]-N-(1-phenylethyl)cyclohexanehexanamide hydrochloride

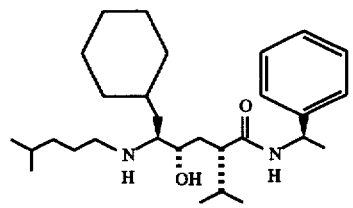

As in Example 27, the Example 12 product is reacted first with α(R)-methylbenzenemethanamine and then 4-methylvaleraldehyde.

Yield=58%; oil; IR (KBr): 3280, 3030, 1640, 1544, 1494, 1386, 1280, 1170, 1062 cm$^{-1}$; MS (ES), 459 (M+H)$^+$.

EXAMPLE 29

[αS-(αR*,γR*,δR*)]γ-hydroxy-α-(1-methylethyl)-δ-[(4-methylpentyl)amino]-N-(2-phenylethyl)cyclohexanehexanamide hydrochloride

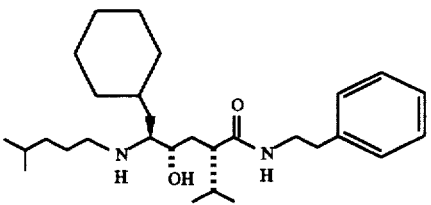

Prepared by treating the Example 12 product with benzeneethanamine and 4-methylvaleraldehyde.

Yield=50%; mp 64°-65° C.; IR (KBr): 3294, 3064, 1638, 1548, 1498, 1468, 1388, 1060 cm$^{-1}$; MS (ES), 459 (M+H)$^+$.

EXAMPLE 30

[αS-(αR*,γR*,δR*)]γ-hydroxy-α-(1-methylethyl)-δ-[(4-methylpentyl)amino]-N-(2-methylpropyl)cyclohexanehexanamide hydrochloride

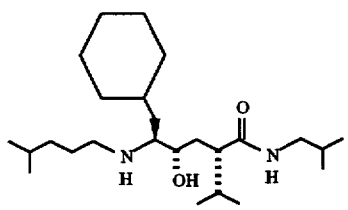

Prepared by reacting Example 12 product with 2-methylpropanamine and then 4-methylvaleraldehyde.

Yield=60%; mp 80°-82° C.; IR (KBr): 3296, 2958, 1640, 1552, 1468, 1368, 1310, 1062 cm$^{-1}$; MS (ES), 411 (M+H)$^+$.

EXAMPLE 31

[αS-(αR*,γR*,δR*)]N-(2,2-dimethylpropyl)-γ-hydroxy-α-(1-methylethyl)-δ-[(4-methylpentyl)amino]cyclohexanehexanamide hydrochloride

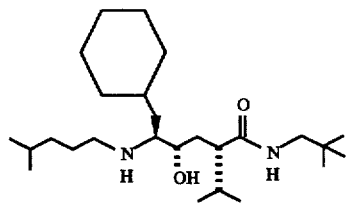

Prepared from Example 12 product, 2,2-dimethylpropanomine and 4-methylvaleraldehyde.

Yield=59%; mp 95°-97° C.; IR (KBr): 3852, 2962, 1688, 1636, 1558, 1474, 1390, 1254, 1126, 1022 cm$^{-1}$; MS (ES), 441 (M+H)$^+$.

EXAMPLE 32

[αS-(αR*,γR*,δR*)]γ-hydroxy-α-(1-methylethyl)-δ-[(4-methylpentyl)amino]-N-[3-(methylthio)propyl] cyclohexanehexanamide hydrochloride

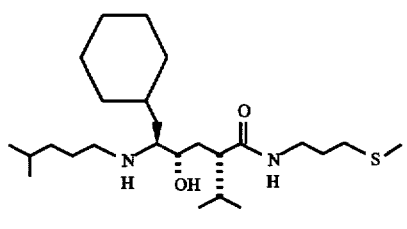

Prepared from Example 12 product, 3-(methylthio) propanamine and 4-methylvaleraldehyde.

Yield=32%; mp 57° C.: IR (KBr) 3278, 2958, 2926, 2870, 2852, 1640, cm$^{-1}$; MS (ES), 443 (M+H)$^+$.

EXAMPLE 33

[αS-(αR*,γR*,δR*)]N-Butyl-γ-hydroxy-α-(1-methylethyl)-δ-[(3-methylpentyl)amino] cyclohexanehexanamide hydrochloride

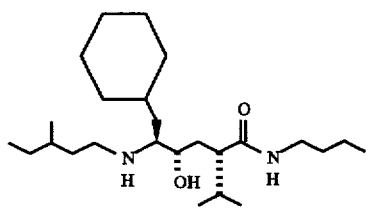

Prepared from Example 12 product, butylamine and 3-methylpentanal.

Yield=59%; mp 67° C.: IR (KBr) 3286, 2960, 2928, 2874, 2856, 1638, cm$^{-1}$; MS (ES), 411(M+H)$^+$.

EXAMPLE 34

[αS-(αR*,γR*,δR*)]N-Butyl-γ-hydroxy-α-(1-methylethyl)-δ-[(5-methylhexyl)amino] cyclohexanehexanamide hydrochloride

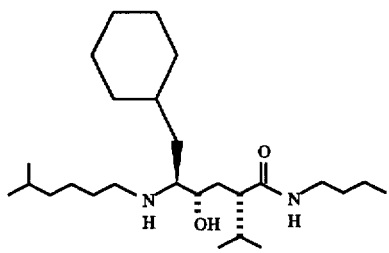

Prepared from Example 12 product, butylamine and 5-methylhexanal.

Yield=62%; mp 68° C.: IR (KBr) 3280, 2928, 2870, 2854, 1636, 1466, cm$^{-1}$; MS (ES), 425(M+H)$^+$.

EXAMPLE 35

[αS-(αR*,γR*,δR*)]N-Butyl-γ-hydroxy-δ-[(3-methylbutyl)amino]-α-(1-methylethyl) cyclohexanehexanamide hydrochloride

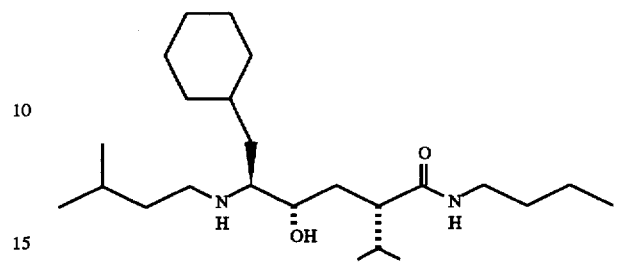

Prepared from Example 12 product, butylamine and 3-methylbutanal.

Yield=52%; mp 95° C.: IR (KBr) 3296, 2960, 2928, 2874, 2854, 1638, cm$^{-1}$; MS (ES), 397 (M+H)$^+$.

EXAMPLE 36

[αS-(αR*,γR*,δR*)]N-Butyl-γ-hydroxy-α-(1-methylethyl)-δ-[[(3-methylphenyl)methyl]amino] cyclohexanehexanamide hydrochloride

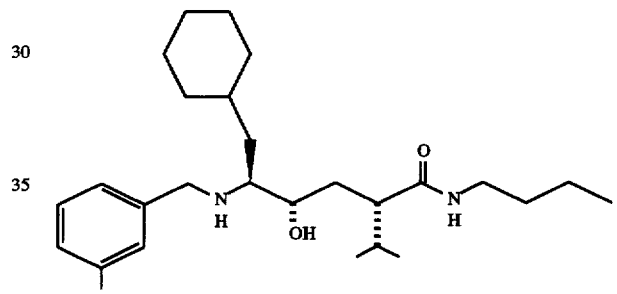

Prepared from Example 12 product, butylamine and 3-methylbenzenecarboxaldehyde.

Yield=60%; mp 136° C.: IR (KBr) 3296, 2960, 2926, 2872, 2854, 1638, cm$^{-1}$; MS (ES), 431 (M+H)$^+$.

EXAMPLE 37

[αS-(αR*,γR*,δR*)]N-Butyl-γ-hydroxy-δ-[[(3-methoxyphenyl)methyl]amino]-α-(1-methylethyl) cyclohexanehexanamide hydrochloride

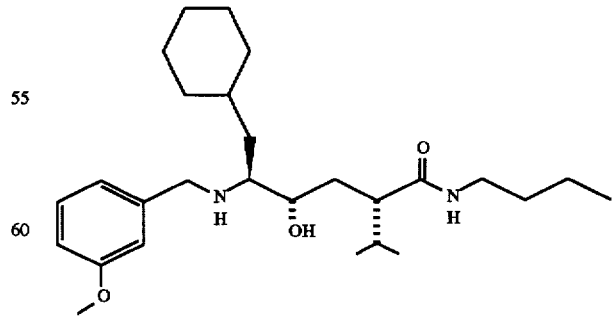

Prepared from Example 12 product, butylamine and 3-methoxybenzaldehyde.

Yield=76%; mp 110° C.: IR (KBr) 3300, 2960, 2928, 2854, 1638, 1268, cm$^{-1}$; MS (ES), 447 (M+H)$^+$.

EXAMPLE 38

[αS-(αR*,γR*,δR*)]N-Butyl-γ-hydroxy-α-(1-methylethyl)-δ-[[(2-naphthyl)methyl]amino] cyclohexanehexanamide hydrochloride

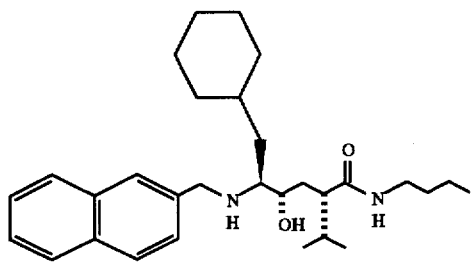

Prepared from Example 12 product, butylamine and 2-naphthalenecarboxaldehyde.

Yield=48%; mp 110° C.: IR (KBr) 3296, 2958, 2926, 2872, 2852, 1638 cm$^{-1}$; MS (ES), 467 (M+H)$^+$.

EXAMPLE 39

[αS-(αR*,γR*,δR*)]N-Butyl-γ-hydroxy-δ-[2-(1-methylethoxy)ethyl]amino]-α-(1-methylethyl) cyclohexanehexanamide hydrochloride

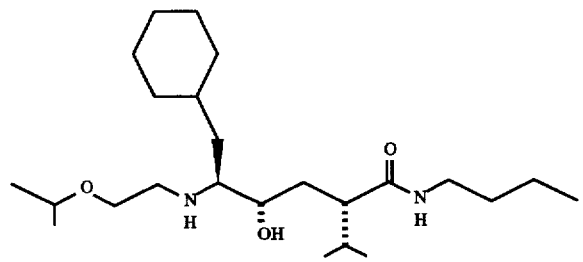

Prepared from Example 12 product, butylamine and 2-(1-methylethoxy)ethanal.

Yield=53%; mp-glass: IR (KBr) 3282, 2960, 2928, 2872, 2856, 1640, cm$^{-1}$; MS (ES), 413(M+H)$^+$.

EXAMPLE 40

[αS(αR*,γR*,δR*)]-γ-Hydroxy-δ-[(4-methylcyclohexyl)amino]-α-(1-methylethyl)-N-(2-methylpropyl)cyclohexanehexanamide

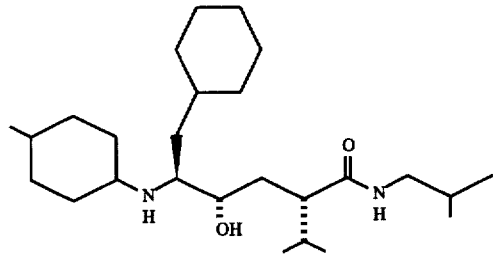

[αR(αR*,γR*,δS*)]-δ-Amino-γ-hydroxy-α-(1-methylethyl)-N-(2-methylpropyl)cyclohexanehexanamide (50 mg, 0.153 mmol) and 4-methylcyclohexanone (19 mg, 0.169 mmol) were dissolved in benzene (10 mL). Ti(iPrO)$_4$ (65 mg, 0.23 mmol) was added and the mixture was refluxed under N$_2$ for 24 h. The mixture was cooled, diluted with 10 mL of EtOH and NaBH$_4$ (12 mg, 0.307 mmol) was added. The mixture was then heated at reflux for 10 h. Water (1 mL) was added and the solvents were removed in vacuo. The residue was dissolved with CH$_2$Cl$_2$, and sequentially washed with dil. Na$_2$CO$_3$ and brine. The organic phase was dried over Na$_2$SO$_4$, filtered, and concentrated in vacuo. Silica gel chromatography (1:0:0 to 9:1:0.1 CH$_2$Cl$_2$:MeOH:NH$_4$OH gradient) of the concentrate afforded the title compound (19 mg, 29%), mp 119° C.

IR (KBr): 3338, 2958, 2924, 2870, 2850, 1644, cm$^{-1}$; MS (ES): 422 (M+H)$^+$.

Analogous to the Example 40 procedure, the following compounds were prepared.

EXAMPLE 41

[αS(αR*,γR*,δR*)]-γ-Hydroxy-δ-[(1,4-dimethylpentyl)amino]-α-(1-methylethyl)-N-(2-methylpropyl)cyclohexanehexanamide hydrochloride

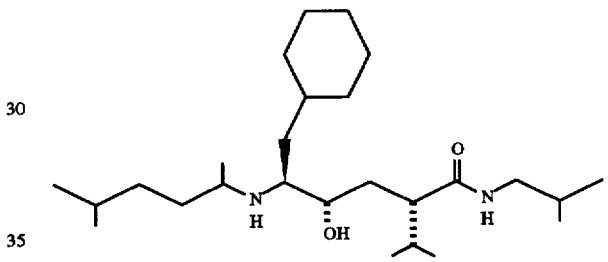

Prepared from 5-methyl-2-hexanone and [αR (αR*,γR*, δS*)]-δ-amino-γ-hydroxy-α-(1-methylethyl)-N-(2-methylpropyl)cyclohexanehexanamide.

Yield=38%; mp 75° ; IR (KBr): 3328, 2960, 2928, 2872, 2854, 1640, cm$^{-1}$; MS (ESI), 424 (M+H)$^+$.

EXAMPLE 42

[αS(αR*,γR*,δR*)]-γ-Hydroxy-δ-[(3-methylcyclohexyl)amino]-α-(1-methylethyl)-N-(2-methylpropyl)cyclohexanehexanamide

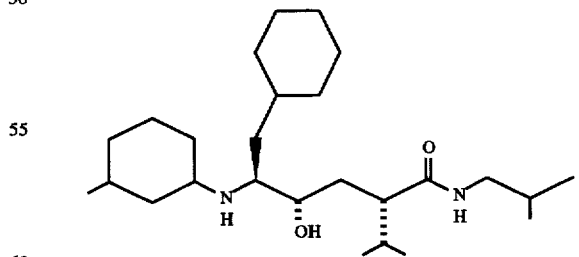

Prepared from 3-methylcyclohexanone and [αR (αR*, γR*,δS*)]-δ-amino-γ-hydroxy-α-(1-methylethyl)-N-(2-methylpropyl)cyclohexanehexanamide.

Yield=33%; mp 192° C.; IR (KBr): 3310, 2958, 2928, 2870, 2854, 1640, cm$^{-1}$; MS (ESI): 422 (M+H)$^+$.

EXAMPLE 43

[αS(αR*,γR*,δR*)]-γ-Hydroxy-δ-[(3-methylcyclopentyl)amino]-α-(1-methylethyl)-N-(2-methylpropyl)cyclohexanehexanamide

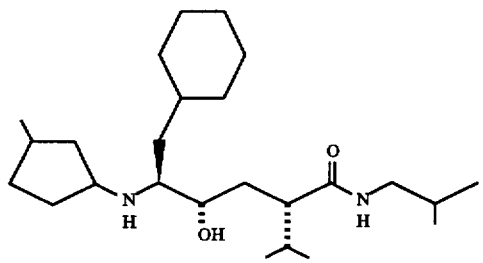

Prepared from 3-methylcyclopentanone and [αR(αR*,γR*,δS*)]-δ-amino-γ-hydroxy-α-(1-methylethyl)-N-(2-methylpropyl)cyclohexanehexanamide.

Yield=5%; mp 89° C.; IR (KBr): 3376, 2958, 2928, 2870, 2854, 1638, cm$^{-1}$; MS (ESI): 408 (M+H)$^+$.

EXAMPLE 44

[αS(αR*,γR*,δR*)]-N-butyl-γ-hydroxy-α-(1-methylethyl)-δ-[[4-(1-methylethyl)cyclohexyl]amino]cyclohexanehexanamide hydrochloride

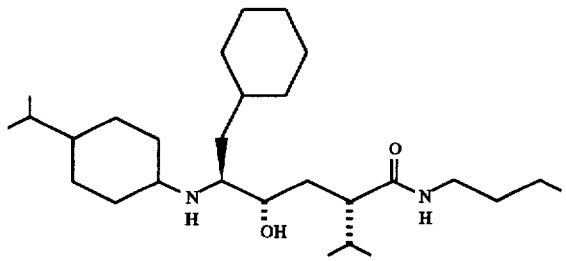

Prepared from 4-(1-methylethyl)cyclohexanone with [αR(αR*,γR*,δS*)]-δ-amino-N-butyl-γ-hydroxy-α-(1-methylethyl)cyclohexanehexanamide.

Yield=38%; mp 69° C.; IR (KBr): 3286, 2958, 2928, 2870, 1636, 1450 cm$^{-1}$; MS (ESI): 450 (M+H)$^+$.

The following compounds were prepared via reductive amination of an amino alcohol with an aldehyde (e.g. the Na(OAc)$_3$BH method of Example 19):

EXAMPLE 45

[αS(αR*,γR*,δR*)]-N-Butyl-γ-hydroxy-α-(1-methylethyl)-δ-(pentylamino)cyclohexanehexanamide hydrochloride

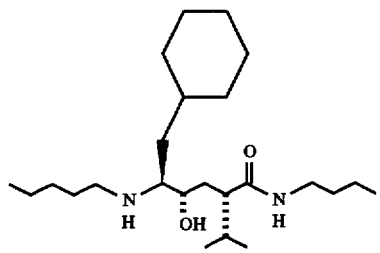

Prepared from pentanal wandith [αR(αR*,γR*,δS*)]-δ-amino-N-butyl-γ-hydroxy-α-(1-methylethyl)cyclohexanehexanamide.

Yield=46%; mp oil; IR (KBr): 3284, 2960, 2928, 2872, 2856, 1638, cm$^{-1}$; MS (ESI): 396 (M+H)$^+$.

EXAMPLE 46

[αS(αR*,γR*,δR*)]-N-Butyl-δ-[(3-cyclopropyl)propyl]amino-γ-hydroxy-α-(1-methylethyl)cyclohexanehexanamide hydrochloride

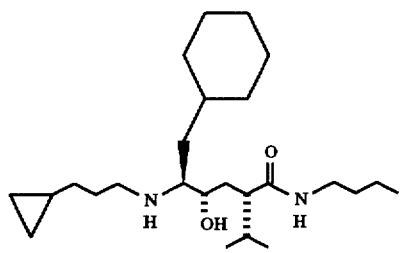

Prepared from cyclopropylpropanal and [αR(αR*,γR*,δS*)]-δ-amino-N-butyl-γ-hydroxy-α-(1-methylethyl)cyclohexanehexanamide.

Yield=38%; mp glass; IR (KBr)3284, 2960, 2928, 2872, 2854, 1638, cm$^{-1}$; MS (ESI), 408 (M+H)$^+$.

EXAMPLE 47

[αS(αR*,γR*,δR*)]-N-Butyl-δ-[(3-cyclopentyl)propyl]amino-γ-hydroxy-α-(1-methylethyl)cyclohexanehexanamide hydrochloride

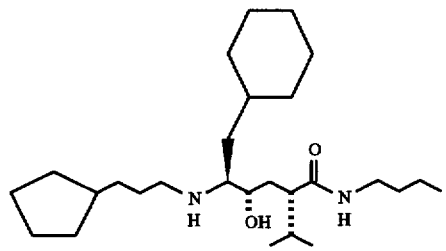

Prepared from cyclopentylpropanal and [αR(αR*,γR*,δS*)]-δ-amino-N-butyl-γ-hydroxy-α-(1-methylethyl)cyclohexanehexanamide.

Yield=64%; mp glass; IR (KBr): 3286, 2956, 2928, 2856, 1638, 1552 cm$^{-1}$; MS (ES), 436 (M+H)$^+$.

EXAMPLE 48

[αS(αR*,γR*,δR*)]-N-Butyl-δ-[(3-cyclohexyl)ethyl]amino-γ-hydroxy-α-(1-methylethyl)cyclohexanehexanamide hydrochloride

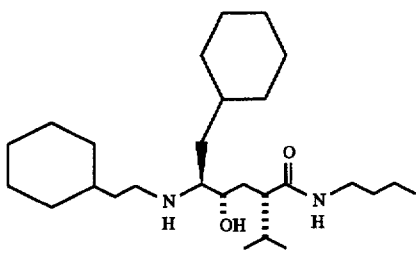

Prepared from cyclohexylethanal and [αR(αR*,γR*,δS*)]-δ-amino-N-butyl-γ-hydroxy-α-(1-methylethyl)cyclohexanehexanamide.

Yield=53%; mp 69° C.; IR (KBr): 3294, 2960, 2926, 2852, 1638, 1448 cm$^{-1}$; MS (ES), 436 (M+H)$^+$.

EXAMPLE 49

[αS(αR*,γR*,δR*)]-γ-hydroxy-α-(1-methylethyl)-δ-[(4-methyl-3-pentenyl)amino]-N-(2-methylpropyl)cyclohexanehexanamide

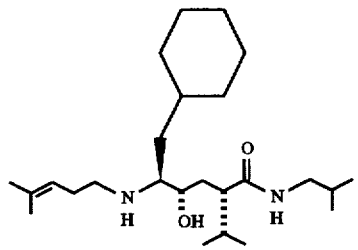

This compound was prepared via alkylation of [αR(αR*,γR*,δS*)]-δ-amino-γ-hydroxy-α-(1-methylethyl)-N-(2-methylpropyl)cyclohexanehexanamide with 5-bromo-2-methyl-2-pentene.

[αR(αR*,γR*,δS*)]-δ-Amino-γ-hydroxy-α-(1-methylethyl)-N-(2-methylpropyl)cyclohexanehexanamide (80 mg, 0.245 mmol), 5-bromo-2-methyl-2-pentene (44 mg, 0.27 mmol), and K$_2$CO$_3$ (250 mg) were dissolved in acetonitrile (10 mL) and stirred at RT for 24 h followed by heating at reflux under N$_2$ for 8 h. The solvents were removed in vacuo. The residue was dissolved with CH$_2$Cl$_2$ and washed with water. The organic phase was dried over Na$_2$SO$_4$, filtered, and concentrated in vacuo. Silica gel chromatography (1:0:0 to 95:5:05 CH$_2$Cl$_2$:MeOH:NH$_4$OH gradient) of the concentrate afforded the title compound (42 mg, 42%) as a wax.

Yield=42%; mp waxy solid; IR (KBr): 3324, 2958, 2924, 2870, 2852, 1642, cm$^{-1}$; MS (ESI): 408 (M+H)$^+$.

EXAMPLE 50

Production and detection of β-AP made by cells in culture. The use of transfected H4 (human neuroglioma) cells stably expressing constructs containing wild-type and mutant forms of β-APP have been used to identify inhibitors of β-AP production. The Swedish variant of β-APP produces 5–7 fold more β-AP than the wild type and is typically used due to its enhanced signal. This result can be shown by standard techniques such as immunoprecipitation of the conditioned medium for $^{35}$S-methionine radiolabeled β-AP from cells in culture previously described by Haass, et al., 1992 and Shoji, et al., 1992, or non-radioactively by enzyme-linked immunosorbent assay (ELISA) as demonstrated by Seubert, et al., 1992. The capture antibody is typically a mouse monoclonal (IgG1/kβ-APPa). The antibody recognizes the carboxyl terminal epitope of β-AP. The specificity of the capture antibody ensures measurement of β-AP without interference by other secreted β-APP fragments that share amino acid sequence (β-AP1-16) with β-AP. The detecting antibody is typically an affinity purified rabbit polyclonal antibody, specific for the amino terminus of β-AP. In the cell-based assay conditioned medium from H4 cells is tested by ELISA for the quantity of β-AP present. The cell-based assay can be used to identify compounds that inhibit β-AP production. The assay should detect agents that inhibit cleavage at the β-secretase and/or the γ-secretase cleavage site as well as detecting any agent that interferes with the production and/or release of β-AP.

A typical ELISA-based assay requires plating of the transfected cells at a density sufficient for the rapid detection of the secreted β-AP (experimentally predetermined for a particular stable cell population) in a 96-well format. Cells are plated for at least six hours prior to the introduction of the test compound at which time the growth medium is replaced by fresh medium containing the agent to be tested. Test agents may typically consist of synthetic compounds, secondary metabolites from bacterial or fungal fermentation extracts, or extracts from plant or marine samples. All synthetic agents are initially screened at doses ranging from 10–100 µM or in the case of extracts at sufficient dilution to minimize cytotoxicity. Incubation of the cells with the test agent will continue for approximately 16 hours at which time equal aliquots of media from each sample well is removed and placed into a previously prepared ELISA plate for β-AP quantitation. The ELISA is carried out in a manner described by others (Haass, et al., 1992; Hawlow and Lane, 1988) and the β-AP signal quantitated. Results are obtained by analysis of the ELISA plate following development and comparison to the mock treated cell populations and samples in which known amounts of β-AP were added to construct a standard concentration curve. A positive acting compound is one which inhibits the β-AP relative to the control sample by at least 50% at the initial tested concentration and does not show cytotoxicity. If a compound is found to be active, then a dose response experiment is performed to determine the lowest dose of compound necessary to elicit the inhibition of the production of β-AP.

TABLE 2

Inhibition of γ-Secretase by Representative Formula I Compounds

| Example | Activity Rating |
|---|---|
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |

TABLE 2-continued
Inhibition of γ-Secretase by Representative Formula I Compounds
| Example | Activity Rating |
|---------|-----------------|
| 31 | +++ |
| 32 | +++ |
| 33 | +++ |
| 34 | +++ |
| 35 | +++ |
| 36 | +++ |
| 37 | ++ |
| 38 | + |
| 39 | + |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
Activity ratings:
+++ < = 10
++ > 10 & < = 25
+ > 25 & < = 50 μM
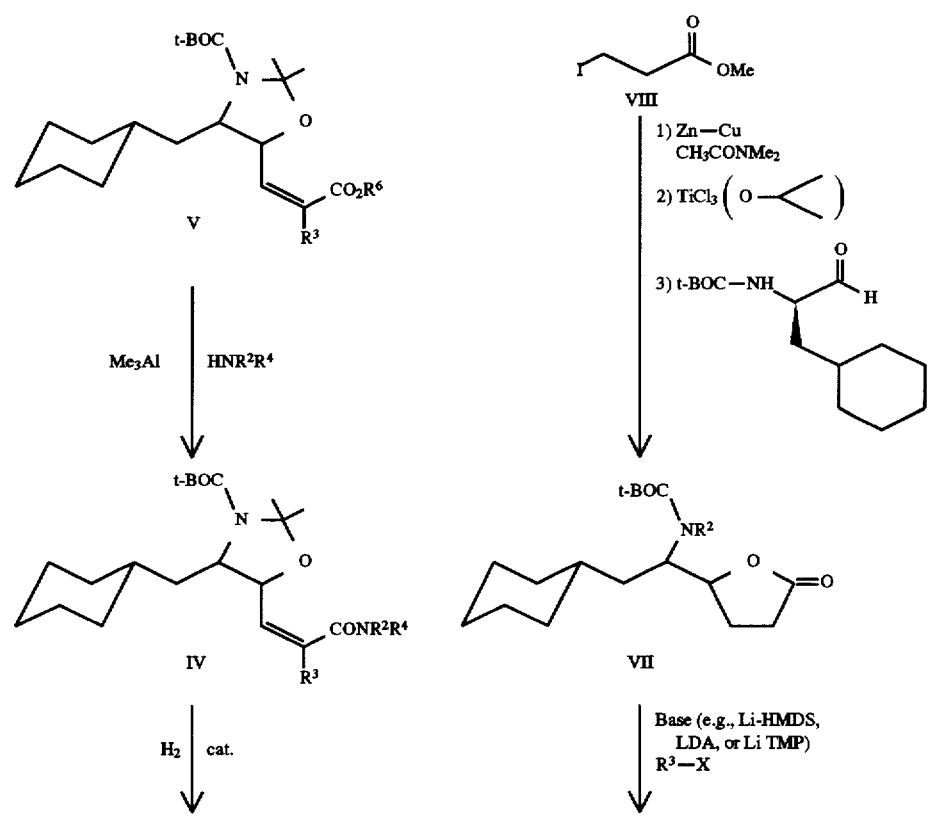
Scheme A
Synthesis of Formula I Compounds -continued
Scheme A
Synthesis of Formula I Compounds
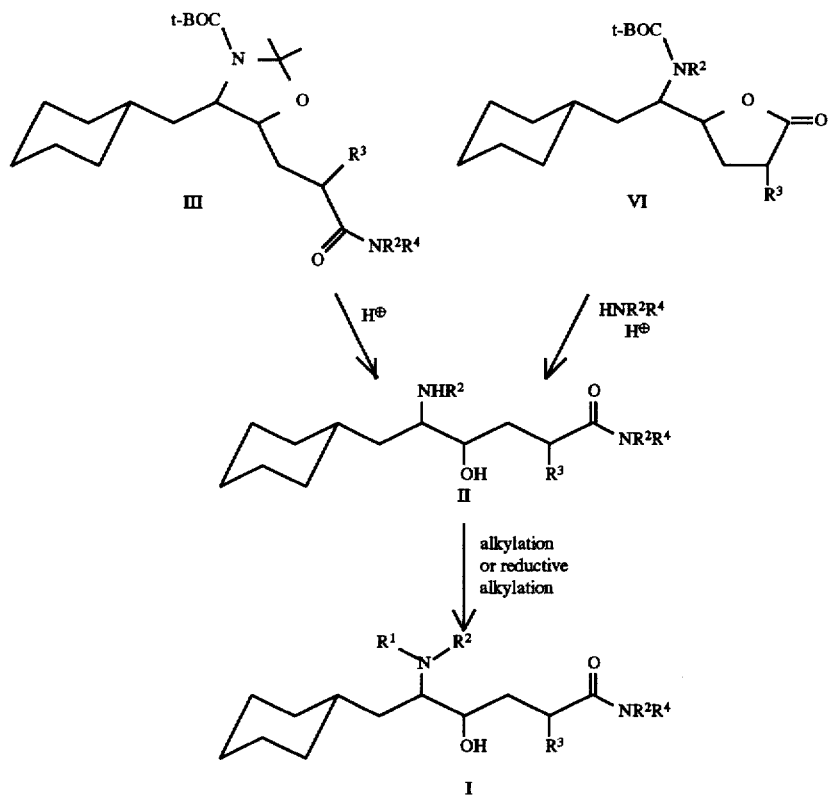
Scheme B
Synthesis of Chiral Compounds of Formula I
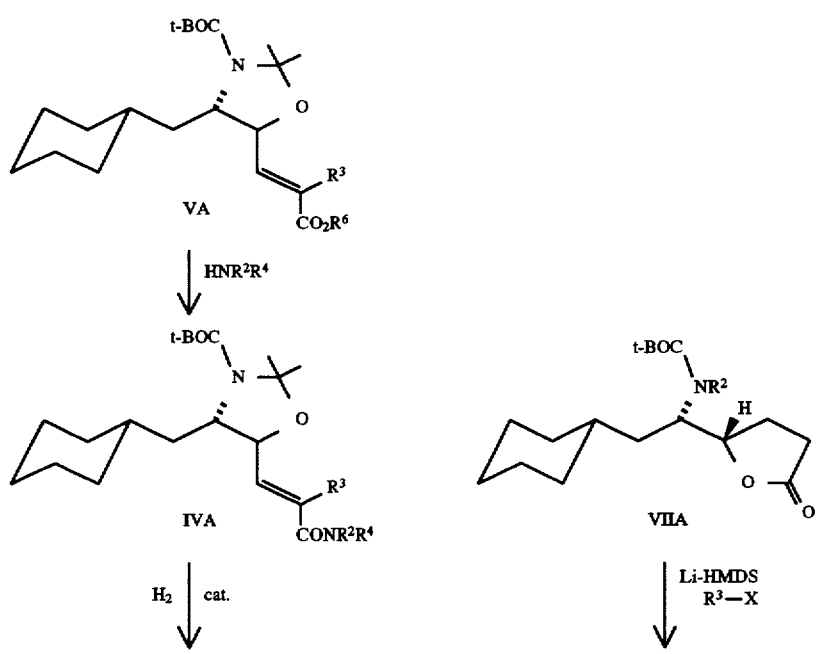

-continued
Scheme B
Synthesis of Chiral Compounds of Formula I
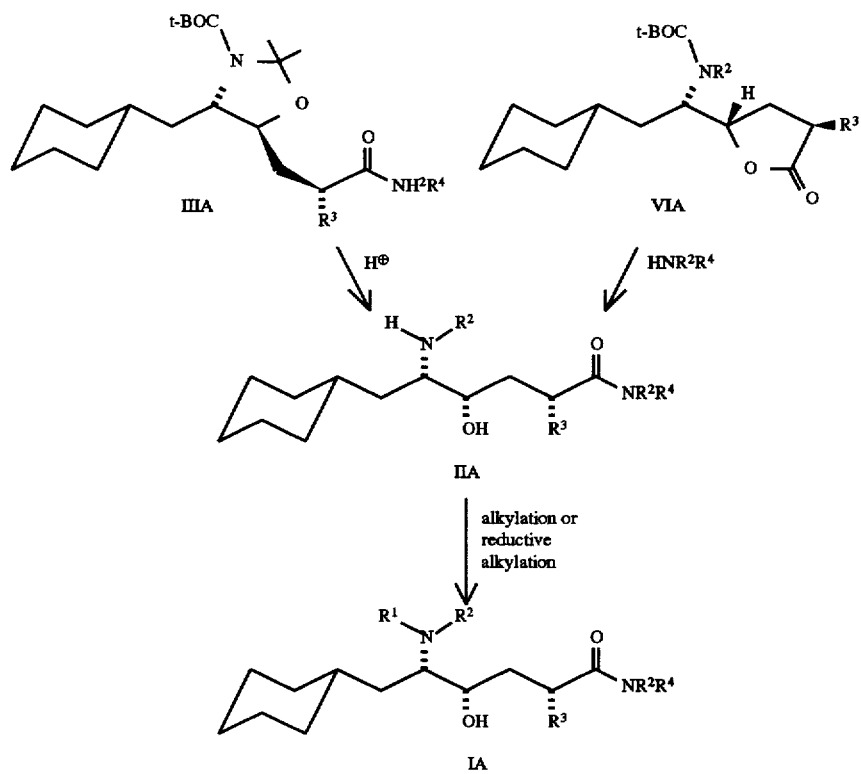
Scheme C
Chiral Synthesis of Formula VI Intermediates
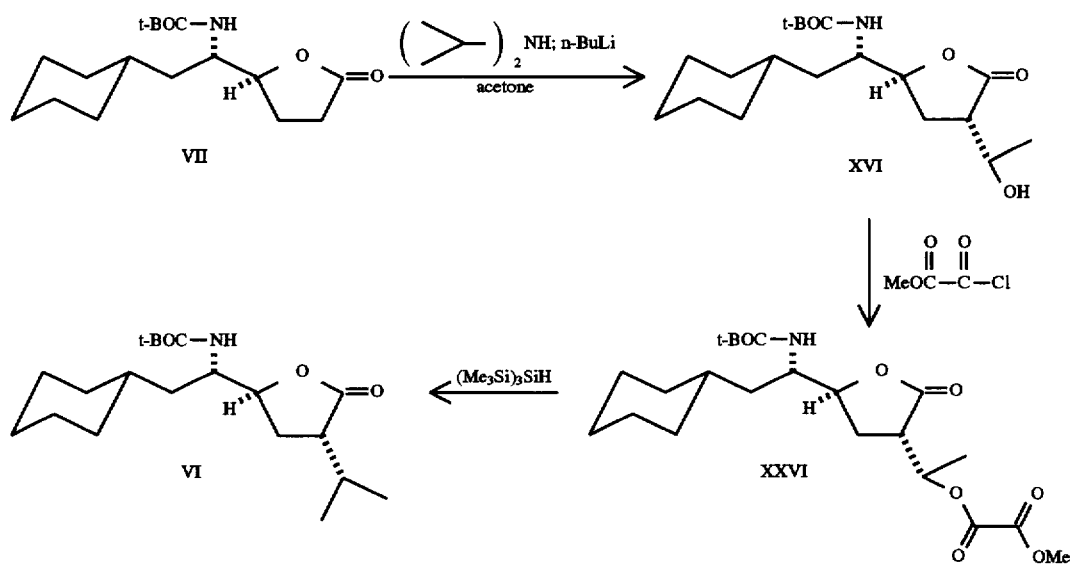

What is claimed is:
1. A compound of Formula I and its pharmaceutically

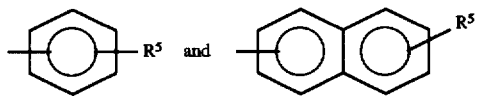

acceptable acid addition salts and hydrates thereof wherein $R^1$ is selected from $C_{4-8}$ alkyl, $C_{4-8}$ alkenyl, $C_{1-4}$ alkoxy-$C_{1-4}$ alkanediyl, $R^5$-substituted $C_{3-6}$ cycloalkyl, $R^5$-substituted $C_{3-6}$ cycloalkyl-lower-alkanediyl, and Ar—$(CH_2)_n$— in which Ar is

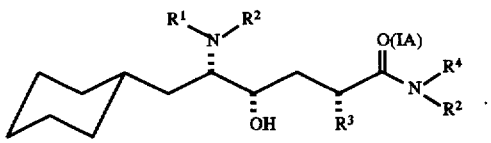

with $R^5$ being hydrogen, lower ($C_{1-6}$) alkyl, and lower alkoxy, and n is 1 to 4;

$R^2$ is independently selected from hydrogen and methyl; $R^3$ is selected from lower alkyl, $C_{3-6}$ cycloalkyl, $C_{3-6}$ cycloalkyl-lower-alkanediyl, $C_{3-6}$ alkenyl, and Ar—$(CH_2)_n$—; and $R^4$ is selected from $R^3$, lower alkyl-thio-lower alkyl, and

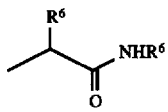

wherein $R^6$ is lower alkyl.

2. A compound of Formula I having the stereochemistry of Formula IA

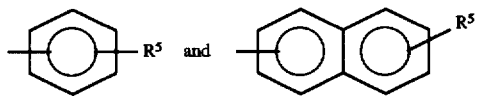

3. A compound of claim 1 wherein $R^1$ is $C_{4-8}$ alkyl or $R^5$-substituted-$C_{3-6}$ cycloalkylalkanediyl; $R^2$ is hydrogen; and $R^3$ is lower alkyl.

4. A compound of claim 2 wherein $R^1$ is $C_{4-8}$ alkyl or $R^5$-substituted-$C_{3-6}$ cycloalkylalkenediyl; $R^2$ is hydrogen; and $R^3$ is lower alkyl.

5. A compound of claim 4 selected from

[αS-(αR*,γR*,δR*)]N-Butyl-γ-hydroxy-α-(1-methylethyl)-δ-[(4-methylpentyl)amino]cyclohexanehexanamide;

[αS-(αR*,γR*,δR*)]N-Butyl-γ-hydroxy-δ-[(4-methylpentyl)amino]-α-(2-methylpropyl)cyclohexanehexanamide;

[αS-(αR*,γR*,δR*)]N-Butyl-γ-hydroxy-δ-[(4-methylpentyl)amino]-α-(2-propyl)cyclohexanehexanamide;

[αS-(αR*,γR*,δR*)]-α-(cyclohexylmethyl)-N-(cyclopropylmethyl)-γ-hydroxy-δ-[(4-methylpentyl)amino]cyclohexanehexanamide;

[αS-(αR*,γR*,δR*, N-(1S*))]γ-hydroxy-α-(1-methylethyl)-δ-[(4-methylpentyl)amino]-N-(1-phenylethyl)cyclohexanehexanamide;

[αS-(αR*,γR*,δR*)]γ-hydroxy-α-(1-methylethyl)-δ-[(4-methylpentyl)amino]-N-(2-phenylethyl)cyclohexanehexanamide;

[αS-(αR*,γR*,δR*)]γ-hydroxy-α-(1-methylethyl)-δ-[(4-methylpentyl)amino]-N-(2-methylpropyl)cyclohexanehexanamide;

[αS-(αR*,γR*,δR*)]N-(2,2-dimethylpropyl)-γ-hydroxy-α-(1-methylethyl)-δ-[(4-methylpentyl)amino]cyclohexanehexanamide;

[αS-(αR*,γR*,δR*)]γ-hydroxy-α-(1-methylethyl)-δ-[(4-methylpentyl)amino]-N-[3-(methylthio)propyl]cyclohexanehexanamide;

[αS-(αR*,γR*,δR*)]N-Butyl-γ-hydroxy-α-(1-methylethyl)-δ-[(3-methylpentyl)amino]cyclohexanehexanamide;

[αS-(αR*,γR*,δR*)]N-Butyl-γ-hydroxy-α-(1-methylethyl)-δ-[(5-methylhexyl)amino]cyclohexanehexanamide;

[αS-(αR*,γR*,δR*)]N-Butyl-γ-hydroxy-δ-[(3-methylbutyl)amino]-α-(1-methylethyl)cyclohexanehexanamide;

[αS(αR*,γR*,δR*)]-γ-Hydroxy-δ-[(4-methylcyclohexyl)amino]-α-(1-methylethyl)-N-(2-methylpropyl)cyclohexanehexanamide;

[αS(αR*,γR*,δR*)]-γ-Hydroxy-δ-[(1,4-dimethylpentyl)amino]-α-(1-methylethyl)-N-(2-methylpropyl)cyclohexanehexanamide hydrochloride;

[αS(αR*,γR*,δR*)]-γ-Hydroxy-δ-[(3-methylcyclohexyl)amino]-α-(1-methylethyl)-N-(2-methylpropyl)cyclohexanehexanamide;

[αS(αR*,γR*,δR*)]-γ-Hydroxy-δ-[(3-methylcyclopentyl)amino]-α-(1-methylethyl)-N-(2-methylpropyl)cyclohexanehexanamide;

[αS(αR*,γR*,δR*)]-N-butyl-γ-hydroxy-α-(1-methylethyl)-δ-[[4-(1-methylethyl)cyclohexyl]amino]cyclohexanehexanamide hydrochloride;

[αS(αR*,γR*,δR*)]-N-Butyl-γ-hydroxy-α-(1-methylethyl)-δ-(pentylamino)cyclohexanehexanamide hydrochloride;

[αS(αR*,γR*,δR*)]-N-Butyl-δ-[(3-cyclopropyl)propyl]amino-γ-hydroxy-α-(1-methylethyl)cyclohexanehexanamide hydrochloride;

[αS(αR*,γR*,δR*)]-N-Butyl-δ-[(3-cyclopentyl)propyl]amino-γ-hydroxy-α-(1-methylethyl)cyclohexanehexanamide hydrochloride;

[αS(αR*,γR*,δR*)]-N-Butyl-δ-[(3-cyclohexyl)ethyl]amino-γ-hydroxy-α-(1-methylethyl)cyclohexanehexanamide hydrochloride; and

[αS(αR*,γR*,δR*)]-γ-hydroxy-α-(1-methylethyl)-δ-[(4-methyl-3-pentenyl)amino]-N-(2-methylpropyl)cyclohexanehexanamide.

6. The compound of claim 5, [αS-(αR*,γR*,δR*)]N-Butyl-γ-hydroxy-α-(1-methylethyl)-δ-[(4-methylpentyl)amino]cyclohexanehexanamide.

7. A method for inhibiting γ-secretase comprising the administration to a host of an effective γ-secretase inhibiting amount of a claim 1 compound.

8. A method for inhibiting β-amyloid protein production comprising the administration to a host of an effective β-amyloid protein inhibiting amount of a claim 1 compound.

9. A pharmaceutical composition comprising a claim 1 compound and a pharmaceutically acceptable carrier.

* * * * *